United States Patent [19]

Jogan et al.

[11] Patent Number: 4,628,748
[45] Date of Patent: Dec. 16, 1986

[54] EFFLUENT SAMPLER

[75] Inventors: Michael J. Jogan, Solon; Kevin T. Kermode, Parma; Tom L. Romick, Mantua; Ken L. Stephen, Seven Hills, all of Ohio

[73] Assignee: The Stouffer Corporation, Solon, Ohio

[21] Appl. No.: 718,730

[22] Filed: Apr. 1, 1985

[51] Int. Cl.⁴ ............................................. G01N 1/00
[52] U.S. Cl. ............................. 73/863.01; 73/864.34
[58] Field of Search ................. 422/79, 63; 73/864.34, 73/864.51, 864.31, 863.82, 864.85, 863.86, 863.01, 863.11, 864.86, 864.91; 366/140; 324/438

[56] References Cited

U.S. PATENT DOCUMENTS

| | | | |
|---|---|---|---|
| 2,122,991 | 7/1938 | Polston | 73/864.34 |
| 2,348,806 | 5/1944 | Gillard et al. | 73/863.11 |
| 2,637,211 | 5/1953 | Norman, Jr. | 73/864.34 |
| 2,703,304 | 3/1955 | Paladino | 366/140 |
| 3,282,113 | 11/1966 | Sachnik | 73/864.91 |
| 3,468,166 | 9/1969 | Putman | 73/864.34 |
| 3,684,702 | 8/1972 | Hartmann | 422/79 |
| 3,838,719 | 10/1974 | Lederer | 141/284 |
| 3,927,701 | 12/1975 | Lederer | 141/98 |
| 3,954,009 | 5/1976 | Lederer | 73/198 |
| 3,994,687 | 11/1976 | Engelbrecht | 422/63 |
| 4,165,643 | 8/1979 | Moll et al. | 73/863.11 |
| 4,262,533 | 4/1981 | Jaeger | 73/863.11 |
| 4,288,308 | 9/1981 | Hach | 422/79 |
| 4,321,544 | 3/1982 | Riseman | 324/438 |
| 4,418,581 | 12/1983 | Jones | 73/864.34 |

Primary Examiner—Stewart J. Levy
Assistant Examiner—Robert R. Raevis
Attorney, Agent, or Firm—Body, Vickers & Daniels

[57] ABSTRACT

A fluid flow sampler having a peristaltic pump which periodically draws a sample volume of effluent from a sewer main through a supply line to a collecting chamber wherein the pH is recorded after which the sampled effluent is transferred to an agitated and cooled holding chamber. The supply lines are valve controlled to delay delivery to the collecting chamber until steady state conditions are achieved in the supply line. The supply lines are air purged when the pump is not operating and lines are underground which are connected to a sampler inside a building thereby eliminating line freezing. The entire operation of obtaining, holding and maintaining the representative samples is programable and completely automatic.

36 Claims, 5 Drawing Figures

EFFLUENT SAMPLER

BACKGROUND OF THE INVENTION

The present invention relates to effluent sampling devices and in particular to an effluent sampler for withdrawing effluent from a remote location for controlled collection and analysis at a central location.

The present invention is particularly suitable for sampling industrial effluent and will be described with particular reference thereto; however, it will hereinafter become apparent that the invention has broader application to the collection of samples from various fluidlines wherein the conveyed fluid contains species, the presence and amounts of which must be periodically ascertained Industrial sites, without captive water purification facilities, must discharge the effluent into municipal sewage lines. The municipal sewage line leads to a waste processing facility whereat the combined municipal effluent is purified. The industrial effluent places a higher pollution load on the facility than residential or business waste. The costs associated with the industrial portion is also considerably higher. However, inasmuch as all the effluent is combined prior to processing, it is not possible for the municipality to allocate processing costs proportionately. In order to more accurately allocate such costs, many municipalities have adopted surcharge regulations which require the discharger or others to assay the effluent at point of discharge to the main sewer line and pay supplemental charges in accordance therewith. Generally, this is accomplished by periodically sampling the discharge on a statistically representative basis and analyzing the samples with regard to certain effluent parameters indicative of the contribution to increased processing costs. On the basis of the analyses and discharged volume, a surcharge is determined in accordance with the municipalities fee schedule.

Typically, the samples are collected at the discharge point on an hourly basis, one day at a time, for a limited number of days each month in order to give a representive hourly and daily profile of the monthly effluent discharge. The collected samples are then analyzed for parameters such as biological oxygen demand (BOD), chemical oxygen demand (COD), oil and grease, suspended solids and pH. On the basis of these figures, the charges are established.

While these samples may be manually collected at point of discharge, more conventionally automatic sampling devices are placed thereat. In one such sampler, a container is lowered into the discharge line through an access hole such as a manhole. The container includes a battery operated sampler that includes a pump which withdraws effluent from the line and on a timed schedule automatically discharges the effluent into a series of containers. At the end of the sampling period, the container is withdrawn from the line, the samples removed and forwarded for analysis. Depending on whether consecutive sampling days are required, the sampler may be repositioned or moved to storage until the next sampling period.

While capable of meeting sampling requirements, many disadvantages and problems are associated with the use and operation of such devices. First, the sampler must be transported to the site for each sampling period. Inasmuch as such site is oftentimes located at a remote location on the industrial site and must be operative during fair and foul weather, the installation and removal time together with the inconvenience and unpleasantness associated therewith are considerable. Further, the raising and lowering of such devices may be beyond the physical capabilities of the technical staff and require assignment of supplemental personnel for this function. Moreover, these samplers are unattended during the sampling period. Should a malfunction occur, it is only determined at the conclusion of the sampling period. Such a faulty sampling may require an additional sampling at a future date thereby disrupting technical schedules, all with consequent inconvenience and additional cost.

Such samplers are particularly prone to malfunction during temperature extremes. During cold periods, for instance, the sampler lines may freeze thereby preventing the sampling schedule. During hot periods, the samples may undesirably deteriorate rendering the subsequent analysis inaccurate. At any time, the lines may plug with foreign material thereby interrupting the sampling. Also, because the effluent samples are directly deposited upon a common diverting chamber, the grease and oil and solids left on the diverting chamber between samples are not purged and therefore are drawn or added to next incoming sample and so collected in individual bottles leading to a non-representative sample and unnecessarily increased surcharge. Purging of the line occurs but is very brief after uptake and not continuous. Thus, when the next sample starts, the submerged effluent from the previous sample could still reside in the tube at the inlet. Even less desirable, any accumulation or buildup of effluent material in the inlet head, upon start-up goes directly to the collecting bottle, via the common diverting chamber which doesn't represent the true effluent. In order to accurately analyze the sample, it is preferable to analyze non-degraded effluent on a regular basis along with other operational abnormalties e.g., pH, temperature, salt concentration, etc. Such determinations are not possible with devices of the above described type and therefore prompt correction is not possible.

BRIEF SUMMARY OF THE INVENTION

The present invention overcomes the above-mentioned problems and difficulties by providing an effluent sampler which may be permanently located indoors at the appropriate industrial laboratory and which withdraws effluent samples from a remote discharge point on a monitored and representative basis with programable automatic controls.

More particularly, the sampler includes a peristaltic pump having a permanently installed, and preferably buried, intake line having an inlet communicating with the discharge point. The pump discharges a metered quantity of effluent on a scheduled basis into a collecting vessel where the pH and temperature and other parameters thereof are recorded. The collecting vessel is heated to minimize grease buildup which could affect subsequent analysis. The sample is then automatically discharged to a temperature controlled holding vessel until conclusion of the sampling routine thereby avoiding sample degradation. The temperature, preferably around 5° C. effectively limits bacterial growth and thus maintains a representative non-degraded BOD load. Contents are gently stirred with a Teflon coated blade to keep the constituents from settling and sticking.

Preparatory to intake, the sampler intake lines are continuously purged with air to thereby provide that the entire sample is from the desired time interval. The indoor location of the sampler, the air purge and burying of the line, eliminates the potential for plugging and freeze-up. To provide for representative sampling, the pump is in operation between intake and drain for a time sufficient to establish steady state conditions at which time various valves are automatically actuated to divert the flow to the collecting vessel. Accordingly, representative samples are reliably withdrawn and collected. Analysis results, performed by an industrial or an independent laboratory, are very representative, prudently obtained and thusly factual.

Accordingly, it is an object of the present invention to provide a fluid sampling device for automatically sampling a remote fluid line in a central location.

Another obJect is to provide an apparatus for remotely collecting effluent samples and maintaining a composite thereof on an automatic basis and under conditions maintaining sample integrity.

BRIEF DESCRIPTION OF THE DRAWINGS

The above and other objects and advantages of the present invention will become apparent to those skilled in the art upon reading the detailed description below taken in conjunction with the accompanying drawings in which.

DETAILED DESCRIPTION OF A PREFERRED EMBODIMENT

Figure 1:
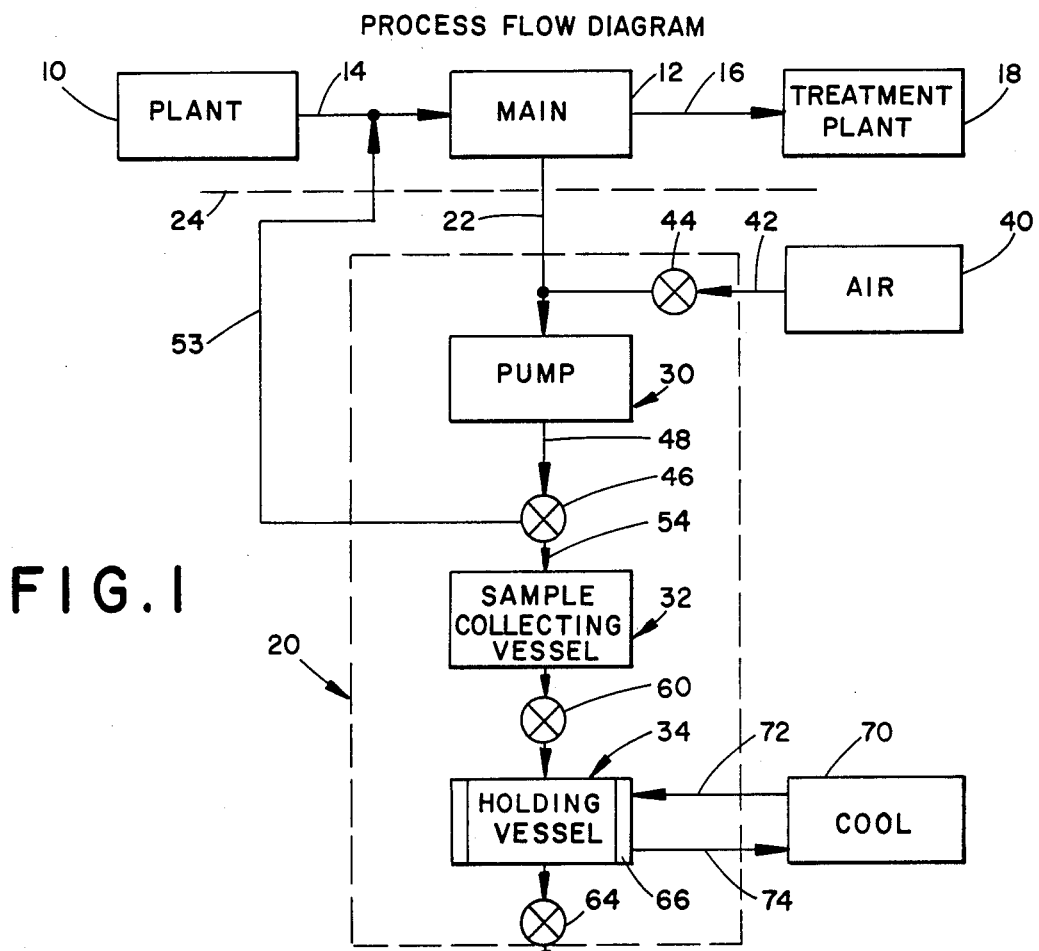
FIG. 1 is a process flow diagram of an effluent sampler in accordance with the invention.

The fluid flow sampler of the present invention finds particular utility in the drawing, sampling and collecting of effluent flow from industrial sites, particularly where quantative and qualitative data must be assembled regarding the flow prior to hook-up with a municipal sewerage system.

Referring to FIG. 1, in such a setting, a plant site 10 discharges effluent from its operations to a sewer main 12 through a main plant drain line 14. The sewer main 12 represents a hook-up connection with the municipal sewerage system line 16 through which combined effluent from other plants, businesses and residences flows to a municipal treatment plant 18. For purposes of determining and allocating processing costs at the treatment plant 18, the municipality may require measurements of certain flow constituents known to present processing burdens on the treatment plant. While such may vary from municipality to municipality and from plant to plant, the more typical constituents will be representatively considered as pollutants constituting biological oxygen demand (BOD), chemical oxygen demand (COD), suspended solids, and oil and grease. Each of the parameters may be identified and quantified in accordance with accepted analytical methodology. Moreover, this methodology must be reliably and statistically representatively performed on periodic samples in order to determine an accurate effluent profile on which to allocate the cost.

To this end, the fluid flow sampler 20, shown within the limits of the dashed lines, automatically withdraws effluent from the main 12 through an intake line 22. The sampler 20 and associated peripheral equipment as hereinafter described, are located within a facility, such as a test laboratory 24, indicated by the dashed lines and which may be located at a substantial distance from the main 12, oftentimes 300 feet or more. The intake line 22 traverses the distance between the main 12 and the effluent sampler 20 in any suitable manner; however a buried location is preferred, particularly when the sampling site is remote from the test laboratory 24. The inlet of the intake line 22 is positioned with respect to the flow where the plant drain line 14 meets the main 12 so as to withdraw a representative sample thereof during sampler operation. The outlet of the intake line 22 is fluidly coupled to the sampler 20 as described below.

The sampler 20 is a portable self-contained unit generally comprising fluidly, in series, a peristaltic pump 30, a collecting vessel 32 and a holding vessel 34. The outlet of the intake line 22 is fluidly connected to the inlet of the pump 30. An in-house air source 40 is connected to the intake line 22 by a branch line 42 having a solenoid controlled two-way valve 44 adjacent the intake line 22. In a first position, the valve 44 is closed blocking air flow through branch line 42. In a second position, the valve 44 is open thereby connecting line 22 with line 42 effecting an air purge of line 22. The outlet of the pump 30 is fluidly connected to an electrically actuated three-way ball valve 46 by line 48. A drain line 53 leads from an outlet of valve 46 to the drain line 14. The valve 46 is connected to the collecting vessel 32 by a line 54. In the second position, the valve 46 is opened and connects the pump 30 to the drain line 53 through line 48. In the first position, the valve 46 is closed and blocks the fluid flow from the pump 30 to drain line 53 and simultaneously connects the pump 30 to the collecting vessel 32 through line 48 and line 54. The valve 46 is conventionally controlled by an electrical actuator 59 shown in dashed lines in FIG. 3.

Figure 2:
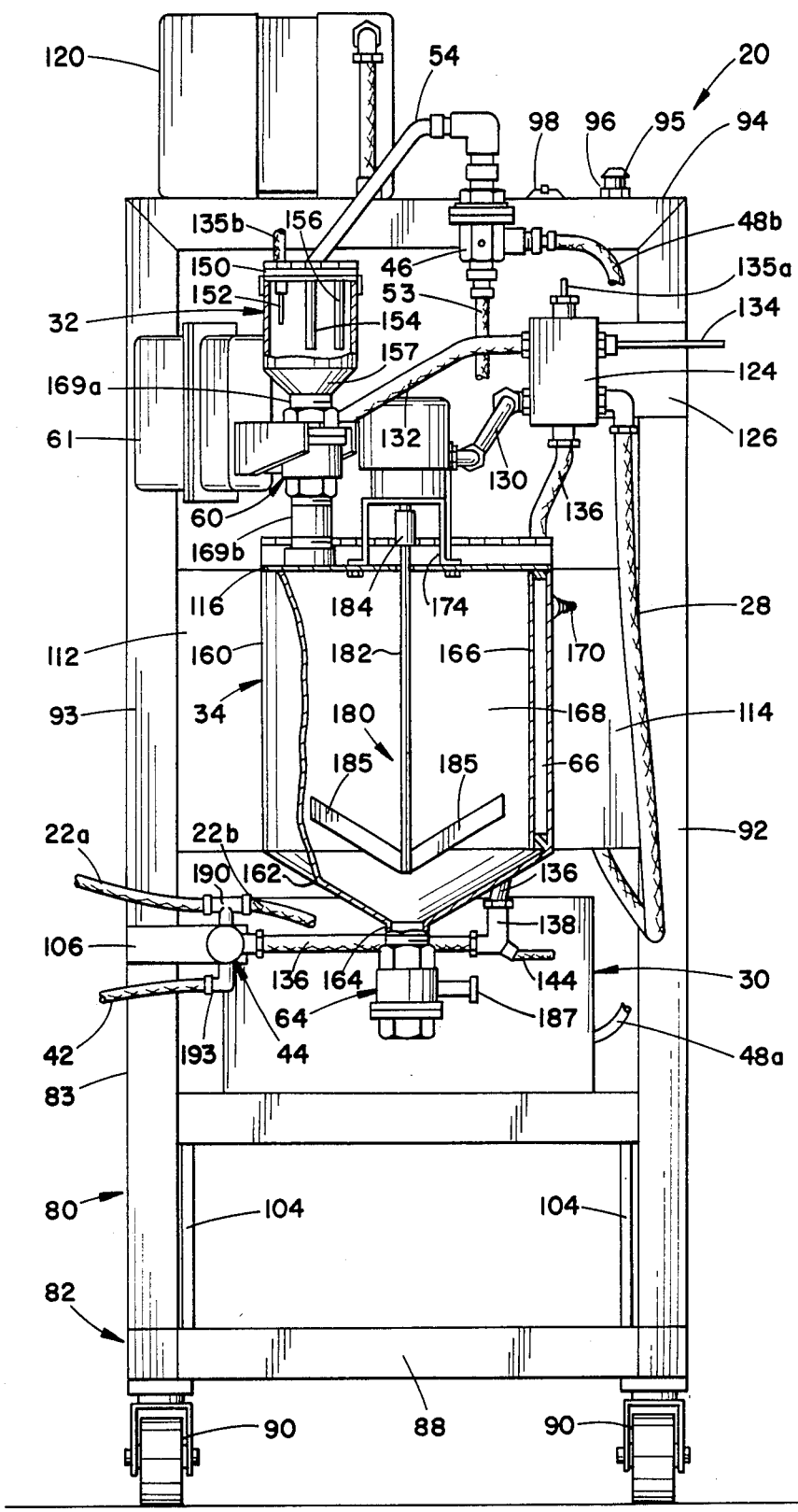
FIG. 2 is a front elevational view of the effluent sampler.

The collecting vessel 32 is fluidly connected to the holding vessel 34 by a ball valve 60 conventionally controlled by an electrical actuator 61 as shown in FIG. 2. In a first position, the valve 60 is closed and blocks flow between the vessels. In a second position, the valve 60 is open and permits gravity fluid flow from the collecting vessel 32 to the holding vessel 34.

The holding vessel 34 is fluidly connected with a sampling vessel 62 by a manually operated ball valve 64. The valve 64 is normally closed and is opened to permit gravity fluid flow from the holding vessel 34 to the sampling vessel 62.

The holding vessel 34 includes an internal cooling chamber 66 which is fluidly connected to a coolant source 70 by inlet line 72 and return line 74.

By means of the control system hereinafter described, the pump 30 and the valves are controlled to selectively establish the desired flow paths for routing the representative effluent sample automatically through the sampler 20 to the vessel 62 for distribution to the appropriate analytical test.

Figure 4:
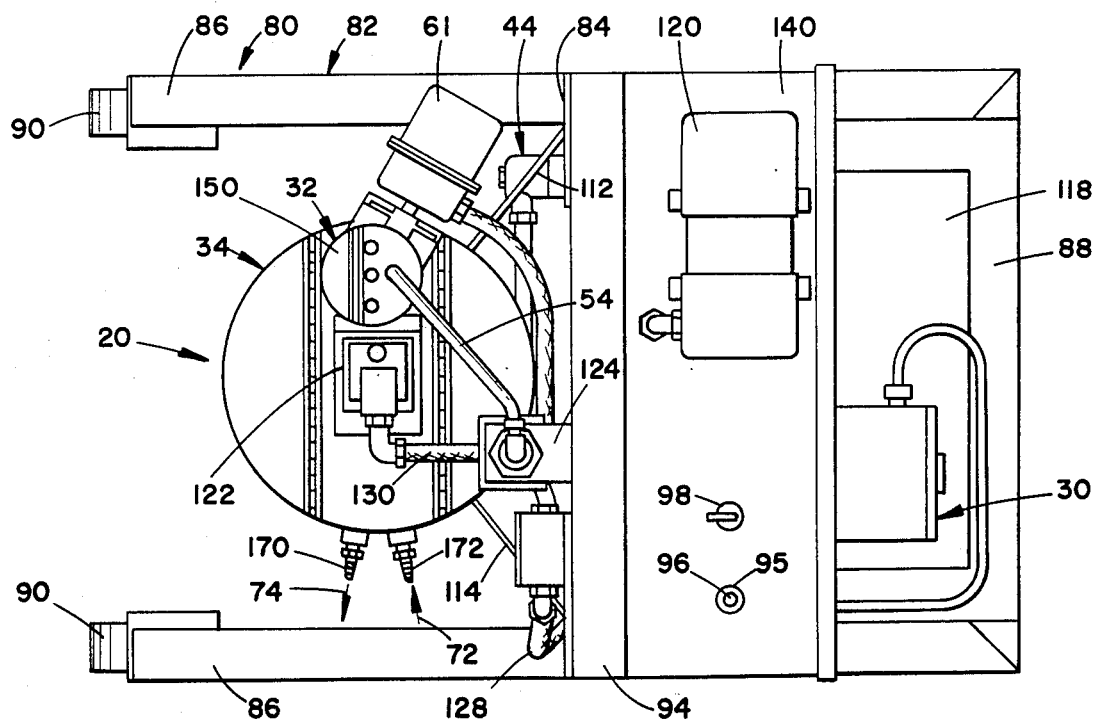
FIG. 4 is a top view of the effluent sampler.
Figure 3:
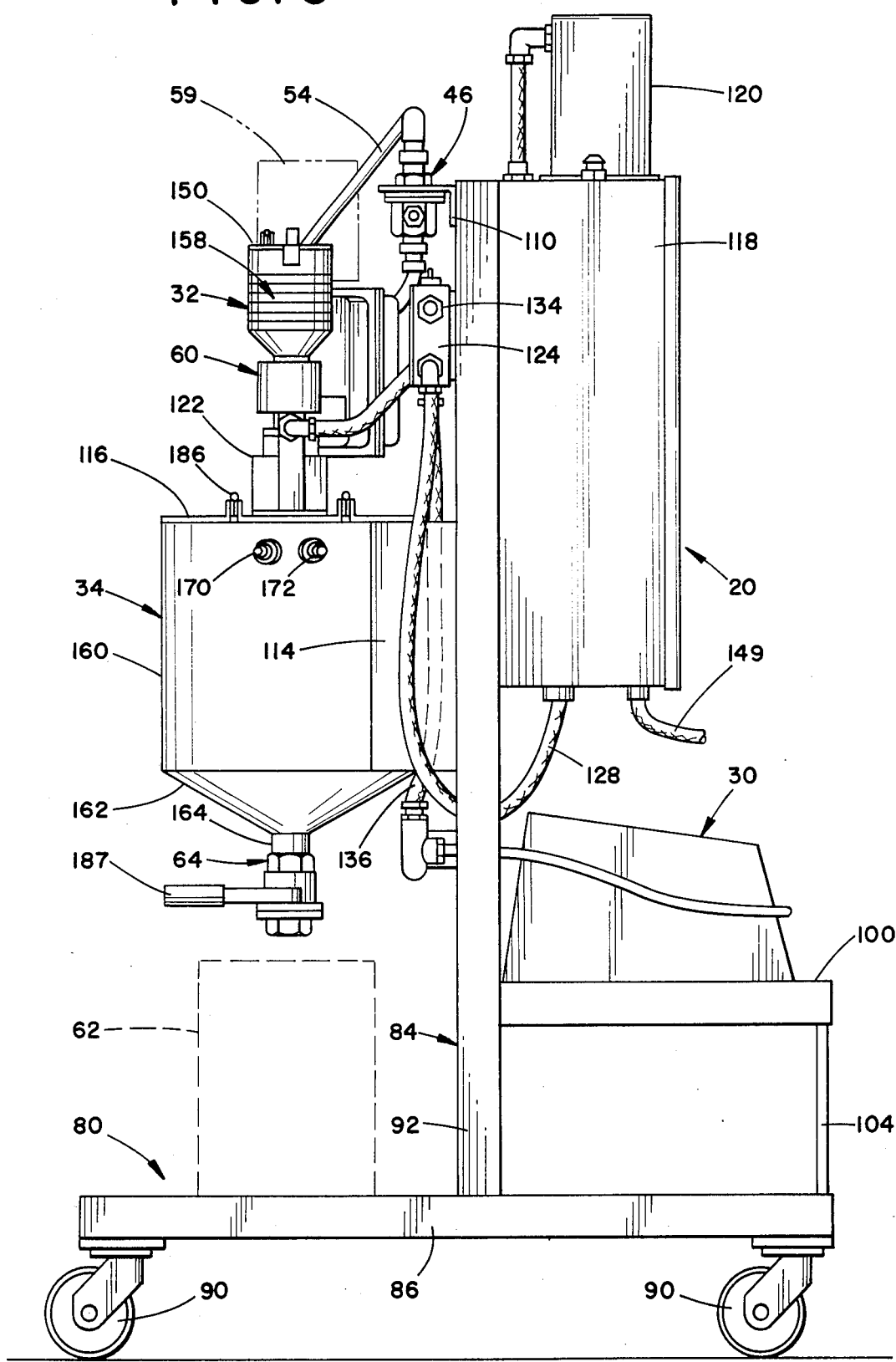
FIG. 3 is a side elevational view of the effluent sampler.

Referring to FIGS. 2 through 4, there shown the fluid flow sampler 20 incorporating the above described fluid flow system. The sampler 20 comprises a mounting frame 80 including a horizontal base frame 82 which centrally supports a vertical frame 84. The base frame 82 comprises two laterally spaced legs 86 interconnected by transverse framing member 88. Four casters 90 are connected at the ends of the leg members 86 and permit the frame to be rolled to desired locations. The vertical frame 84 comprises a pair of vertically extendng arms 92 and 93 connected at their lower ends to the legs 86. The top end of the vertical arms 92 and 93 are interconnected by a top framing member 94. A start switch 95 including a power indicator light 96 and a selector switch 98 are carried on the top surface of framing member 94. A horizontal platform 100 is supported at the rear of the sampler 20. The platform 100 is connected at its front end to the rear of the arms 92 of the vertical frame 84 and vertically supported by posts 104 on the base frame 82.

The pump is carried by the platform 100. The valve 44 is frontally mounted on the lefthand arm 93 of the vertical frame 84 by plate 106.

The valve 46 is mounted on a horizontal top frame member 94 by plate 110. The holding vessel 34 is fixedly mounted on the arms 92 of the vertical frame 84 by means of rearwardly diverging vertical support plates 112 and 114.

The valve 60 and the collecting vessel 32 are supported by the cover 116 of the holding vessel 34. An electrical panel 118 is fixedly mounted on the upper rear faces of the vertical frame 94 above the pump 30. A transformer 120 is mounted on the top surface of the power panel. An electric motor 122 is supported by the cover 116 and the holding vessel 34 adjacent the valve 60. A junction box 124 is supported on the right arm 92 of frame 84 by mounting plate 126. The power panel 118 has a power lead 149 leading to a suitable electrical outlet in the laboratory. An electrical conduit 128 extends between the power panel 118 and the junction box 124 for control purposes as hereinafter described. The junction box 124 has branch conduits 130, 132, 134 respectively leading to the motor 122, the electrical actuator 61 of valve 60 and the electrical actuator 59 of valve 46. The junction box 124 has a signal lead 135 leading to level probe 152. The junction box 124 further has a conduit 136 leading to valve 44 through junction box 138. The junction box 138 has a power lead 144 leading to pump 30.

The collecting vessel 32 comprises a thin walled, cylindrical body defining a chamber and having a lower frusto-conical portion 157 terminating with a threaded pipe 169a which is fixedly and fluidly connected to the inlet of the valve 60. The collection vessel 32 has a hinged cover 150 which supports a vertically adjustable level sensor 152, a pH probe 154 and a thermocouple 156 (FIG. 2), all of which extend downwardly into the collecting chamber.

A temperature compensated pH meter, not shown, is electrically coupled to the probe 154 and the thermocouple 156. The pH meter is continuously energized at an external power outlet. A printer, not shown, is connected to the pH meter for recording the pH strength read by the meter under the control of the sampler control system as described below. The pH meter and the printer are a suitable commercially available design and may be located adjacent to the sampler 20. Alternatively, the pH meter and/or the printer may be directly carried by the sampler 20.

Electrical heating tape 158 in FIG. 3 is wrapped around the cylindrical body of the vessel 32 and is electrically connected to an external power supply.

The holding vessel 34 is a thin walled, cylindrical shell 160 having a lower frusto-conical section 162 terminating with a threaded pipe 164 which is connected to the inlet of the valve 64. The shell includes an inner cylindrical sleeve 166 in spaced relationship to the outer shell and defining outwardly the coolant chamber 66 and inwardly a holding chamber 168. Fluid fittings 170, 172 are mounted on the wall in fluid communication with the chamber 66. The fittings 170, 172 are connected to the lines 72 and 74 leading to the coolant source 70. The motor 122 is mounted on the cover 116 by a bracket 174. A mixing blade 180 extends through a central opening in the cover 116 and includes a vertical shaft 182 fixedly connected to the drive shaft of the motor 122 by a coupling 184. The mixing blade 180 includes vertically inclined blades 185 symmetrically attached to the end of the shaft 182 and are spaced from the base of the vessel 34. The mixing blade 180 is coated with polytetrafluorethylene to prevent adhesion of oil and grease thereto. The valve 60 is fluidly connected to the chamber 168 and structurally supported by a pipe connection 169 on the cover 116. The cover 116 includes hinges 186 for permitting access to the chamber of the collecting vessel 34. The valve 64 includes a manually operable handle 187. In the horizontal position, the valve 64 is closed. In a downwardly rotated position of the handle 187, the valve 64 is open and the contents of the vessel 34 are discharged into the sampling vessel 62 as shown in dotted lines in FIG. 3. The vessel components are preferably constructed of 304 stainless steel for minimizing corrosion.

Referring to FIG. 2, the fluid lines to the sampler 20 are illustrated. The effluent inlet line 22 has a first section 22a extending from the main 12 to a T-fitting 190 on the outlet port of valve 44 and leading from the fitting as section 22b to the inlet of the pump 30. The outlet line 48a from the pump 30 is connected to the inlet port of the valve 46. The airline 42 is connected to the inlet port of valve 44 by a fitting 193. The drain line 53 is connected to one of the outlet ports of the valve 46. The outlet line 54 from the valve 46 projects downwardly into the collecting chamber for discharge thereinto. Three-eights inch I.D. plastic tubing is preferably used for the fluid lines and allows for a rapid sampling of the effluent from the sewer main via the peristaltic pump.

Figure 5:
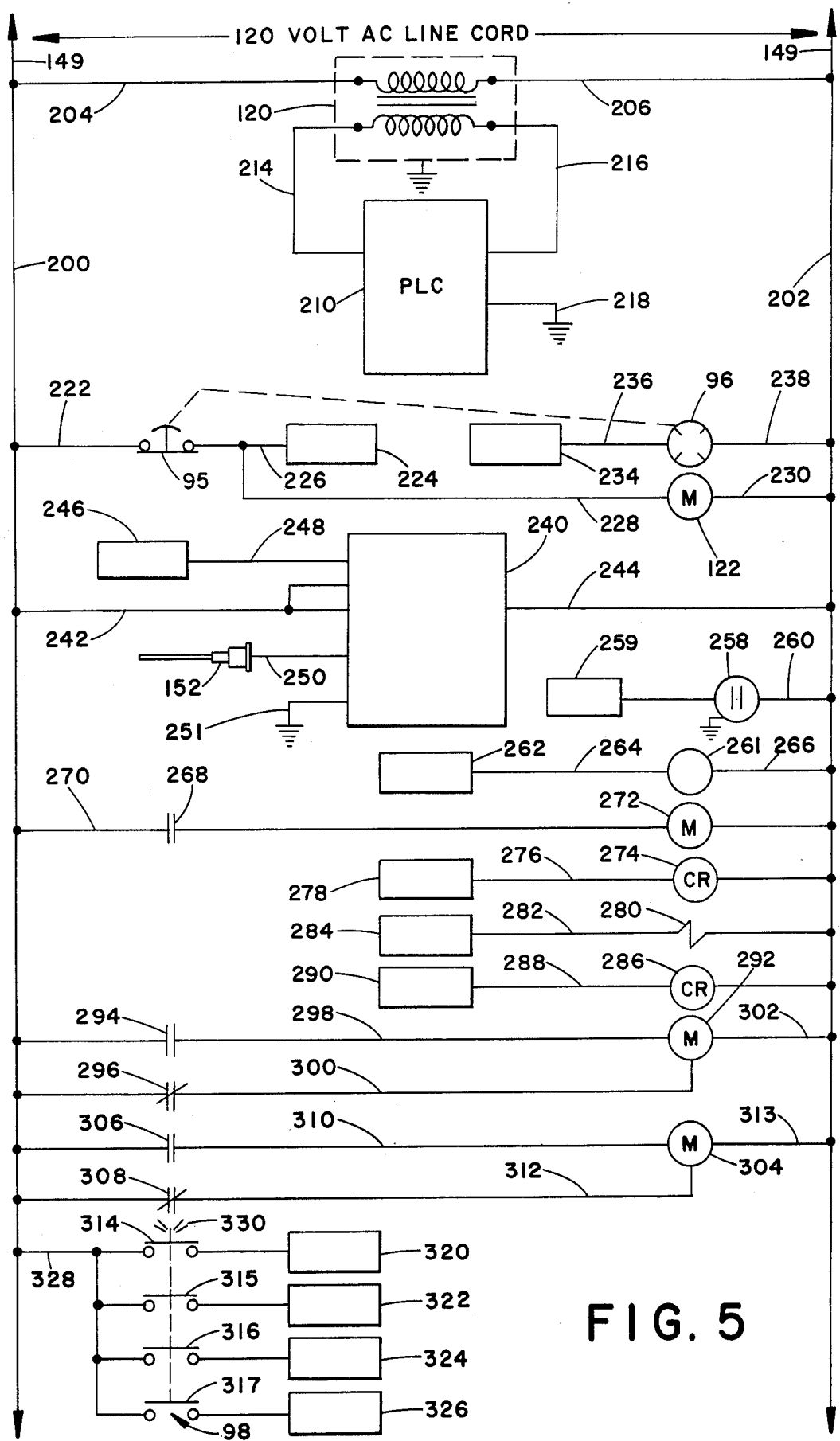
FIG. 5 is a schematic drawing of the control system for the effluent sampler

Referring to FIG. 5, there is shown the electrical control system for the fluid flow sampler described above. Therein, the power cord 149 is electrically connected to terminal blocks 200 and 202 in the electrical panel 118. The input of the transformer 120 is connected to block 200 by line 204 and to block 202 by line 206. The output of the transformer 120 is connected to the power supply of a programable logic controller 210 by lines 214 and 216. The controller 210 is grounded at 218. The transformer 120 serves to provide a constant line voltage to the control system.

The push-pull start switch 95 is connected to block 200 by line 222 and to program input 224 by line 226. The mixer motor 122 is connected by line 228 to line 226 and to block 202 by line 230. The power indicator light 96 is connected between program output 234 and block 202 respectively by lines 236 and 238. A liquid level sensor 240 is connected between blocks 200 and 202 by lines 242 and 244. A high level input 246 is connected to the level sensor 240 by line 248. The level probe 152 is connected to the level sensor by line 250. The level sensor 240 is grounded at 251. The heating tape 158 is connected to an external source, not shown. The pH meter is connected at a grounded outlet, not shown. The printer 258 is connected between program output 259 and block 202 by line 260. The pump motor contactor 261 is connected to program output 262 and block 202 by lines 264 and 266. Normally open contact 268 responsive to the contactor 261 is connected between blocks 200, 202 by line 270 in series with the motor 272 of pump 30. The output 262 is also programmed to open if an inadequate volume of effluent is not received in the collecting chamber within a predetermined time, indicative of a blockage in the inlet line. The control relay 274 for the actuator of valve 46 is connected by line 276 between the program output 278 and block 202. The solenoid 280 for valve 44 is connected by line 282 between program output 284 and block 202. The control relay 286 for the actuator of valve 60 is connected by line 288 between program output 290 and block 202. If an inadequate volume is received in the collecting chamber within a predetermined time, the solenoid 280 is energized to initiate an air purge through the inlet line for a predetermined time for clearing line blockage after which the cycle is resumed. After a certain number of unsuccessful attempts to free the blockage, the pump is shut down to prevent motor burnout while the apparatus associated with the holding vessel is continued thereby maintaining the contents already received. The actuator 292 for the valve 60 is connected in parallel with normally open contacts 294 and normally closed contacts 296 by lines 298 and 300, respectively and with block 202 by line 302. The contacts 294 and 296 are operated by control relay 286. The actuator 304 for valve 46 is connected with normally open contacts 306 and normally closed contact 308 by lines 310 and 312 respectively. The contacts 306 and 308 are respectively controlled by relay 274. The actuator 304 is connected to block 202 by line 313. The time selector switch 98 is conventional and comprises contact switches 314, 315, 316 and 317 which are respectively connected to program inputs 320, 322, 324 and 326. Switch 98 is connected to block 200 by line 328. The selector contacts are selectively closed by control knob 330.

In operation, to initiate the sampling cycle, the selector knob 330 of the selector switch 98 is positioned to close one of the selector switch contacts representing the time interval desired between the effluent sampler collection. In this respect, the contacts may provide for timing cycles of 15 minutes, 30 minutes, 1 hour or two hours. They are also adapted for programming other sampling intervals. Thereafter, the switch 95 is pulled closed to start the cycle and the program timer in response to input 224. Concurrently, the output 234 illuminates the power light 96 and the motor 122 is energized to initiate aggitation of the mixer blade 180 in the holding vessel 34. Alternatively, the control of the motor 122 may be provided in accordance with output from the controller 210. The heating tape 158 is externally energized and serves to maintain the sampling vessel walls at a temperature which prevents build-up of grease and oil thereon. A predetermined time after start of the cycle and subsequently for each sampling interval, the output 262 energized the contactor 261 to close contact 268 thereby energizing the pump motor 272 and initiating the withdrawal of effluent from the main 12 through line 22 to the pump input. Simultaneously, for throughput operation, output 278 leaves contact relay 274 deenergized to keep contact 308 closed and 306 open whereby the actuator 304 operates valve 46 to permit the output from the pump 30 to flow through line 48 to drain line 53. After a predetermined time sufficient to permit the pumping of a representative effluent sample through line 22 and flush line 48 of any prior accumulations, the output 278 energizes the relay 274 closing contact 306 and opening contact 308 reversing the actuator 304 to shift valve 46 to connect the pump 30 to the collecting vessel 32 through lines 48, 54 at which time the collecting chamber fills with effluent as delivered by the pump 30. As the collecting vessel 32 fills to the predetermined level as sensed by level probe 152, the input 246 will initiate the sequencing of the next sampling cycle and completion of the transfer as follows. If an adequate volume is not reached, output 284 energizes solenoid 280 to open valve 44 for one minute and air purge the inlet line 22 and thereby remove any blockage therein, at which time the cycle is resumed. Simultaneously, output 262 is deenergized to deactivate contactor 261 and open contact 268 which in turn stops the pump motor 272. After two attempts, the cycle is terminated while maintaining the holding chamber function. After the predetermined time interval sufficient to stabilize fluid conditions in the collecting vessel 32, an external outlet for pH is used, which in turn is recorded by the printer 258 as controlled by output 259. When the high level is sensed by input 246, output 262 is deenergized to deactivate the contactor 261 open contact 268 and in turn stop the pump motor 272. Concurrently, the output 284 deenergizes solenoid 280 to open valve 44 and initiate air purge of the line 22. After a predetermined time, output 290 is energized to operate relay 286 reversing contacts 294, 296 thereby energizing actuator 292 to open valve 60 thereby draining the effluent sample from the collecting vessel 32 to the holding vessel 34. At predetermined times thereafter, output 290 deenergizes relay 286 reversing the contacts 294, 296 to reverse actuation of the actuator 292 thereby closing valve 60 to complete the cycle. Continuously until initiation of the next cycle as determined by the setting of the selector switch 98, the air purge of the fluid lines continues. As the program timer indicates the next succeeding cycle, the aforementioned sequencing of controls will occur and thereafter repetitively until completion of the full collecting routine. Throughout the sampling routine, coolant from the coolant source 70 flows through reservoir 66 via lines 72 and 74 and is effective for maintaining the contents in the holding chamber at a temperature which retards the growth of any effluent organisms, preferably at a temperature of around 5° C. or less. At the completion of the routine, the output 234 will be operative to pulse the power light 96 indicating completion of the sampling routine. Such pulsing also occurs if the cycle is terminated because of malfunctioning. Thereafter, the switch 95 is manually opened to deactivate the system. Alternatively, automatic controls may be provided to deenergize the system at the completion of the sampling routine.

The time cycles related to the above identified functions may be varied in accordance with the situations involved for the effluent being sampled. However, an initial pump flow is desirable for sufficient time to enable a steady state sample of effluent to be drawn through the intake line and presented to the system. Similarly, the amount of effluent sampled will be in accordance with the needs for subsequent analysis but should be a sufficient volume to enable statistically acceptable information. Volume collected per cycle is adjustable to 500 ml. maximum capacity. Additionally, the purge mode need not be continuously maintained, however it has been found that this is a preferable and acceptable mode for accurate sampling. In other words, the purge may preceed each sampling and follow each sampling sufficient to drain the lines of effluent between cycles and to assure that the intake lines and supply lines are free of effluent before actual sampling for the next cycle commences. Similarly, the timing for operation of the valve 60 to discharge the sample to the holding vessel need only be effected prior to the initiation of the subsequent cycle. However, inasmuch as the holding vessel is maintained under controlled temperature conditions, it is preferable to discharge the effluent sample therein as soon as possible after the pH readings have been taken and the supply line purged. Further, it will be apparent that other valve types may be provided to effect the aforementioned flow control conditions. In this connection, plug valves and ball valves also can be used to selectively divert the flow in the above described manner.

It should also be apparent that the sampler may be provided with other data specific probes for measuring, in addition to pH, other parameters of the collecting vessel effluent. Regardless of the specific instrumentation employed, the fluid flow sampler is effective for automatically collecting on a periodic basis fluid samples from a remote location, providing desired data contemporaneously with the sampling and safely maintaining the integrity of the composite sample until completion of the sampling routine.

We claim:

1. A portable effluent sampler for periodically withdrawing and collecting representative effluent flowing through a waste water stream, comprising:
    a holding vessel including an upwardly opening holding chamber having a lower drainage opening;
    a manually operated valve connected to said drainage opening for blocking fluid flow therethrough in a first position and permitting gravity drainage of the contents in said holding chamber in a second position;
    a collecting vessel including an upwardly opening collecting chamber having a downwardly opening outlet;
    a liquid level sensing means projecting into said collecting chamber;
    a drainage conduit having an upper end connected to said outlet of the collecting vessel and a lower end registering with said holding chamber;
    an actuator controlled first valve fluidly connected in said drainage conduit and movable between a closed position blocking fluid flow through said drainage conduit and an open position permitting fluid flow through said drainage conduit and gravity drainage of the contents of said collecting chamber into said holding chamber;
    an electric powered pump having an inlet and an outlet;
    an electrical switch operatively connected to said pump;
    an inlet line having a first end connected to said inlet of said pump and a second end adapted to be positioned in said waste water stream;
    an outlet line communicating said pump outlet and the upper end of said collecting chamber;
    a drainage conduit communicating to said waste water stream;
    an actuator controlled second valve in said outlet line said second valve having a first position permitting flow of fluid from said pump through said outlet line for delivery into the collecting vessel and a second position blocking fluid flow into said collecting vessel and permitting fluid flow from said outlet line into said drainage conduit;
    an actuator controlled third valve in said inlet line said third valve having an inlet port adapted to be connected to a source of pressurized air, said third valve having a closed position blocking flow of pressurized air through said inlet line and an open position permitting the flow of pressurized air through said inlet line; and,
    a control means operatively connected to said liquid level sensing means and adapted to open and close said switch and to actuate and deactuate said first, second and third valves in a sequential manner, thereby: (a) energizing said pump while maintaining said third valve in the closed position and said second valve in said second position whereby liquid is withdrawn from the waste water stream and discharged through said outlet line and said drainage conduit for a predetermined period of time until a representative waste water sample is presented to said pump, then (b) switching said second valve to said first position whereby said pump is effective to deliver waste water through said outlet line and past said second valve for delivery into said collecting chamber, then (c) sensing when the level of fluid in said collecting chamber reaches a predetermined amount, then (d) closing said switch to deenergize said pump, then (e) opening said third valve to deliver pressurized air through said inlet line to purge said inlet line after said collecting chamber reaches said predetermined amount and until said pump is reenergized, then (f) opening said first valve after the fluid in said collecting chamber reaches said predetermined level in a predetermined time to permit drainage of the contents of said collecting chamber into said holding chamber, then (g) closing said first valve and then, (h) commencing repetition of the sampling cycle a predetermined time after the initiation of the previous sampling cycle.

2. The effluent sampler as recited in claim 1 including an electric motor supported by said holding vessel and having an output shaft driving a mixer blade operable by said control means during said sampling cycle for mixing the contents in said holding chamber.

3. The effluent sampler as recited in claim 2 wherein said holding vessel includes a hinged lid on which said drainage conduit and said collecting vessel are supported, said lid having a hinged section permitting access to said holding chamber.

4. The effluent sampler as recited in claim 2 wherein said holding chamber includes a coolant reservoir adapted to be connected to a source of liquid coolant for cooling the contents in said holding chamber.

5. The effluent sampler as recited in claim 4 wherein said coolant reservoir is effective for maintaining said contents at a temperature of 4° C.

6. The effluent sampler as recited in claim 1 including a probe member carried by said collecting vessel and projecting into said collecting chamber, said probe member being effective for measuring a parameter of the contents in said collecting chamber after said predetermined amount of waste water has been delivered thereto.

7. The effluent sampler as recited in claim 6 wherein said probe member is a temperature compensated pH probe for measuring the pH of said contents at a predetermined time after deenergization of said pump.

8. The effluent sampler as recited in claim 6 wherein electrical heating means carried by the collecting vessel are effective for heating the inner surfaces of the collecting vessel above a temperature at which greases and oils can collect thereon.

9. The effluent sampler as recited in claim 6 wherein said collecting vessel includes a hinged lid from which said probe members are supported and having a hinged section permitting access to said collecting chamber.

10. The effluent sampler as recited in claim 1 wherein said frame member includes roller members vertically supporting the mounting frame for movement along a horizontal surface from one location to another.

11. The portable effluent sampler as recited in claim 1 wherein said control means opens said third valve permitting flow of pressurized air through said inlet line if said predetermined volume is not obtained in said predetermined time.

12. The portable effluent sampler as recited in claim 11 including reenergization means associated with said control means whereby said electrical switch is closed to reenergize said electric powered pump means following purging of said inlet line.

13. The portable effluent sampler as recited in claim 12 including means for limiting said reenergizing of said pump to a predetermined number of repetitions to avoid damage to said pump.

14. The portable effluent sampler as recited in claim 1 wherein the length of said inlet line is in excess of 50 feet.

15. The effluent sampler as recited in claim 1 wherein said electric powered pump means is a peristaltic pump.

16. A fluid flow sampler for obtaining a fluid sample from a source, comprising:
first vessel means;
a liquid level sensing means projecting into said first vessel means;
pump means having an inlet and an outlet;
an electrical switch operatively connected to said pump means for energizing and deenergizing said pump means;
an inlet line fluidly connecting the source with the inlet of said pump means;
an outlet line fluidly connecting the outlet of said pump means with said first vessel means;
first valve means in said outlet line having a first position blocking fluid flow to said first vessel means and a second position permitting fluid flow through said outlet line to said first vessel means;
a branch line associated with said first valve means and fluidly connected with said outlet line when said first valve means are in said first position;
control means operatively connected to said liquid level sensing means and said electrical switch for energizing said pump means with said first valve means in said first position and maintaining said pump means energized when said valve means is in said second position until a predetermined amount of fluid sample enters said vessel means during a predetermined time and for thereafter denergizing said pump means; and
a second vessel means fluidly connected to said first vessel means by a first conduit, and second valve means fluidly connected in said first conduit and operated by said control means for permitting fluid flow from said first vessel means after said predetermined amount of fluid sample has been delivered to said first vessel means during said predetermined time.

17. The fluid flow sampler as recited in claim 16 including third valve means fluidly connected with said inlet line and operated by said control means for admitting pressurized air to said inlet line when said pump means are deenergized for purging the fluid in said inlet line.

18. The fluid flow sampler as recited in claim 17 including fourth valve means fluidly connected with said second vessel means for draining the contents thereof.

19. The fluid flow sample as recited in claim 18 wherein said fourth valve means are manually operated.

20. The fluid flow sampler as recited in claim 18 including timer means operatively associated with said control means for sequencing said control means through repetitive cycles.

21. The fluid flow sampler as recited in claim 17 wherein said control means deenergizes said pump if a predetermined volume of fluid has not been obtained in said first vessel within a predetermined time.

22. The fluid flow sampler as recited in claim 21 including means including said third valve means for purging said inlet line by permitting flow of pressurized air therethrough if said predetermined volume is not obtained in said predetermined time.

23. The fluid flow sampler is recited in claim 22 including reenergization means associated with said control means whereby said electrical switch means is closed to reenergize said pump means following purging of said inlet line.

24. The fluid flow sampler as recited in claim 23 including means for limiting said reenergizing of said pump to a predetermined number of repetitions to thereby avoid damage to said pump.

25. The fluid flow sampler as recited in claims 16 or 20 wherein said first valve means comprises a first valve member fluidly connected in said outlet line adjacent said first vessel means, said first valve member in said first position blocking fluid flow through said outlet line to said first vessel means and permitting fluid flow from said pump means to said branch line and in said second position permitting fluid flow through said outlet line to said first vessel means and preventing fluid flow through said branch line.

26. The fluid flow sampler as recited in claim 25 including heating means for heating the inner surfaces of said first vessel means.

27. The fluid flow sampler as recited in claim 16 wherein said pump means is a peristaltic pump.

28. The fluid flow sampler as recited in claim 27 wherein said third valve means are fluidly connected with said inlet line adjacent said inlet of said peristaltic pump.

29. The fluid flow sampler as recited in claim 16 wherein probe means in said first vessel means are operative when said predetermined amount of liquid is delivered to measure a parameter of the fluid sample.

30. The fluid flow sampler as recited in claim 29 wherein recorder means operatively associated with said probe means record the value of the measured parameter.

31. The fluid flow sampler as recited in claim 30 wherein said probe means is a pH probe.

32. The fluid flow sampler as recited in claim 31 wherein said pH probe is temperature compensated.

33. The fluid flow sampler as recited in claim 30 wherein said recorder means is a printer.

34. The fluid flow sampler as recited in claim 29 including motor driven means for mixing the collected fluid samples in said second vessel means during said repetitive cycle.

35. The fluid flow sampler as recited in claim 34 wherein said second vessel means includes heat exchange means adapted to be connected to a liquid coolant source for cooling the collected fluid samples therein.

36. The fluid flow sampler as recited in claim 16 wherein said control includes means for controlling the time interval of said sampling cycles.

* * * * *